United States Patent [19]

Rustin

[11] Patent Number: 4,751,746
[45] Date of Patent: Jun. 21, 1988

[54] COMBINATION EAR PROTECTOR AND SUNSHIELD ATTACHMENT FOR GLASSES

[76] Inventor: Robby J. Rustin, 3305 Palm Ave., Manhattan Beach, Calif. 90266

[21] Appl. No.: 945,480

[22] Filed: Dec. 23, 1986

[51] Int. Cl.⁴ ............................................. A61F 9/04
[52] U.S. Cl. ........................................... 2/13; 2/449; 2/209; 351/123; 351/47
[58] Field of Search .................. 2/449, 450, 448, 426, 2/13, 209; 351/123, 122, 119, 118, 47

[56] References Cited

U.S. PATENT DOCUMENTS

| | | | |
|---|---|---|---|
| 138,894 | 5/1873 | Isidor | 2/209 |
| 139,831 | 5/1873 | Stone | 2/209 |
| 145,168 | 12/1873 | Goge | 2/209 |
| 993,620 | 5/1911 | Quinn | 2/209 |
| 1,117,968 | 11/1914 | De Bobory | 2/426 |
| 1,621,629 | 4/1926 | Dawson | 2/448 |
| 3,173,147 | 12/1963 | Gross et al. | 2/452 |
| 3,204,252 | 9/1965 | Herrington, Sr. | 2/13 |
| 3,226,729 | 1/1966 | Fucci | 2/12 |
| 3,458,866 | 8/1969 | De Man | 2/450 X |
| 3,856,007 | 12/1974 | Leight | 128/152 |
| 3,932,031 | 1/1976 | Johnston | 2/13 X |
| 3,993,403 | 11/1976 | Brown | 351/178 |
| 4,133,604 | 1/1979 | Fuller | 351/123 |
| 4,682,374 | 7/1987 | Geiser | 2/449 X |

FOREIGN PATENT DOCUMENTS

| | | | |
|---|---|---|---|
| 0609004 | 11/1960 | Canada | 351/47 |
| 0652728 | 11/1937 | Fed. Rep. of Germany | 2/13 |
| 0574301 | 3/1958 | Italy | 351/123 |
| 586868 | 12/1958 | Italy . | |
| 356552 | 10/1930 | United Kingdom . | |

Primary Examiner—Peter Nerbun
Attorney, Agent, or Firm—Charles E. Brown; Charles A. Brown

[57] ABSTRACT

A protector which may be readily mounted on a temple of glasses. The protector will extend from the front of the glasses to and beyond the ear piece of the temple so that there will be protection against wind and sun for one's eyes, the side of the face and one's ears. Preferably the protector is formed of a cloth having insulating characteristics and may include an inner rear panel which together with a rear portion of an outer panel defines an ear receiving pocket into which the rear and top portion of one's ear may be tucked for protection. The outer panel is provided with a sleeve arrangement for receiving the temple and this sleeve arrangement may be in the form of spaced short sleeves or elongated sleeves.

14 Claims, 1 Drawing Sheet

COMBINATION EAR PROTECTOR AND SUNSHIELD ATTACHMENT FOR GLASSES

This invention relates in general to new and useful improvements in attachments for glasses, particularly sunglasses and goggles having temples.

The invention most particularly relates to a protector that may be attached to existing glasses and goggles of the type having temples and are mounted primarily on the temples so as to extend from the lens area of the glasses to a point behind the ear. The protector provides for ear protection against the elements (cold and wind) in addition to wind protection for the eyes and the side of the face. The protector is so constructed and configurated so as to be comfortable to wear while being fully functional and at the same time stylish and can be worn without disturbing one's hair.

The protector is primarily formed of a cloth material having insulating characteristics and in a preferred embodiment, the protector includes an outer panel and a rear inner panel with the rear portion of the outer panel and the rear inner panel together defining an ear receiving pocket which will engage behind a wearer's ear while the temple of the glasses is engaged over one's ear.

Several types of mounting means may be provided with all of the mounting means being in the form of a sleeve for receiving a temple of the associated glasses. Further, the lower front corner of the outer panel may be provided with a suitable clip for engaging a lower corner of the glasses.

With the above and other objects in view that will hereinafter appear, the nature of the invention will be more clearly understood by reference to the following detailed description, the appended claims, and the several views illustrated in the accompanying drawing.

Figure 1:
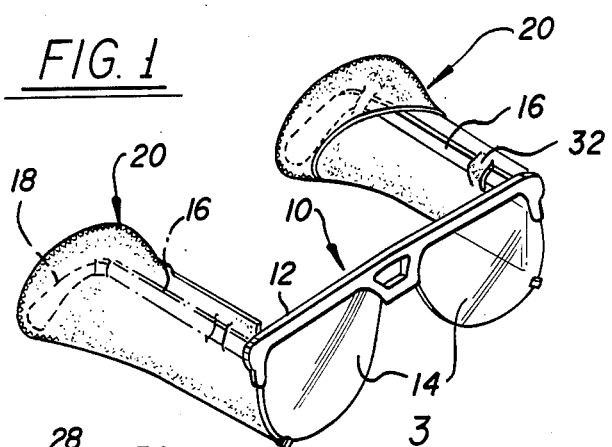
FIG. 1 is a perspective view of sunglasses having mounted on temples thereof protectors in accordance with the invention.

Referring now to the drawings in detail, it will be seen that there is illustrated in FIG. 1 a typical pair of glasses generally identified by the numeral 10. The glasses may either be of the type for normal viewing or sunglasses depending upon the desire of the wearer. The illustrated glasses include a frame 12 carrying a pair of lens 14. The frame 12 has extending rearwardly from each upper corner thereof a temple 16 which terminates in an ear piece 18. A protector, formed in accordance with this invention, is carried by each of the temples 16. Each protector is generally identified by the numeral 20.

Figure 3:
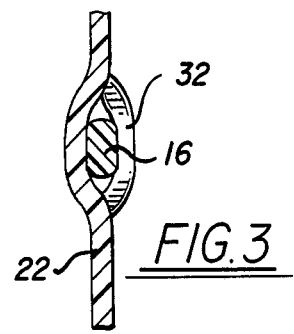
FIG. 3 is an enlarged fragmentary transverse vertical sectional view taken generally along the line 3—3 of FIG. 2 and shows the specific details of a short sleeve for engaging a temple.
Figure 2:
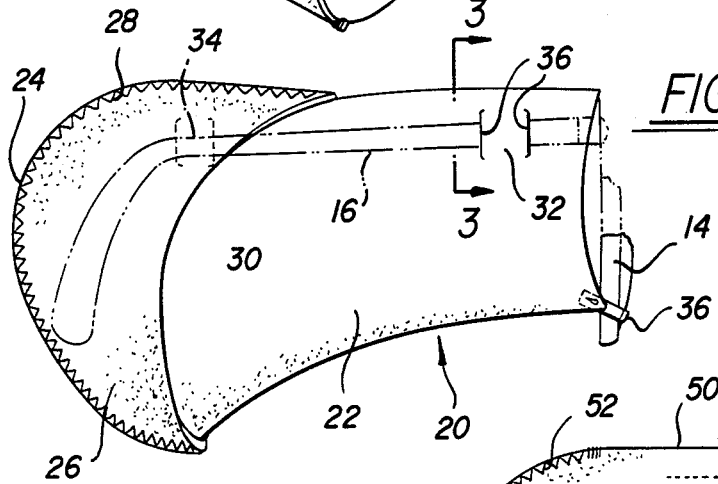
FIG. 2 is an enlarged elevational view looking from the inside of a typical protector constructed for engagement with a temple and with a lower corner of glasses, the temple and glasses being shown in phantom lines.

Referring now to FIGS. 2 and 3, it will be seen that the protector 20 includes an outer panel 22 which is of a length to extend from a respective lens 14 pass a wearer's ear. A rear edge 24 of the panel is curved generally in accordance with the shape of one's ear.

The protector 20 also includes an inner rear panel 26 which is of a configuration matching the rear part of the outer panel 22. The inner panel 26 is secured about its periphery to the like periphery of the outer panel 22 by suitable securing means such as stitching 28. The joined together inner panel 26 and the rear portion of the outer panel 22 define an ear receiving pocket 30 which is open at the front and is of a size and shape to be engaged over the rear portion and top of a wearer's ear.

In order to facilitate the mounting of the protector 20 on an eyeglass temple 16, the outer panel 20 is provided with sleeve means. The sleeve means shown in FIGS. 2 and 3 are in the form of very short straps 32, 34. Each of the straps 32, 34 is defined by a pair of cuts 36. The engagement of the temple 16 within the short sleeve defined by the strap 32 is best shown in FIG. 3.

In order that the lower part of the outer panel 22, particularly at the forward end thereof, be tightly engaged with a typical lens 14 or the side of the frame 12, the lower front corner of the outer panel 22 is provided with a clip 36 which engages the lens of the frame in the manner best shown in FIGS. 1 and 2.

It is to be understood that the protector 20 may be mounted on the temple of the glasses 10 simply by passing the temple through the slots defining the strap 32 and thereafter through the slots defining the straps 34.

In use, the glasses 10 are utilized in the normal manner with the ear pieces 18 of the temple 16 engaging behind a wearer's ear while one's ears are tucked in the ear receiving pockets 30.

Figure 5:
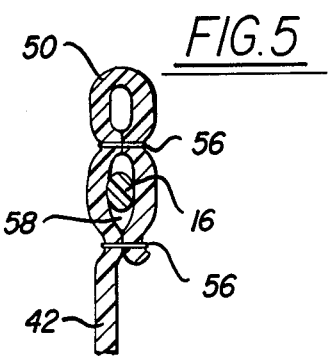
FIG. 5 is an enlarged fragmentary transverse vertical sectional view taken generally along the line 5—5 of FIG. 4 and shows the mounting of the protector on a temple utilizing an elongated sleeve thereof.
Figure 4:
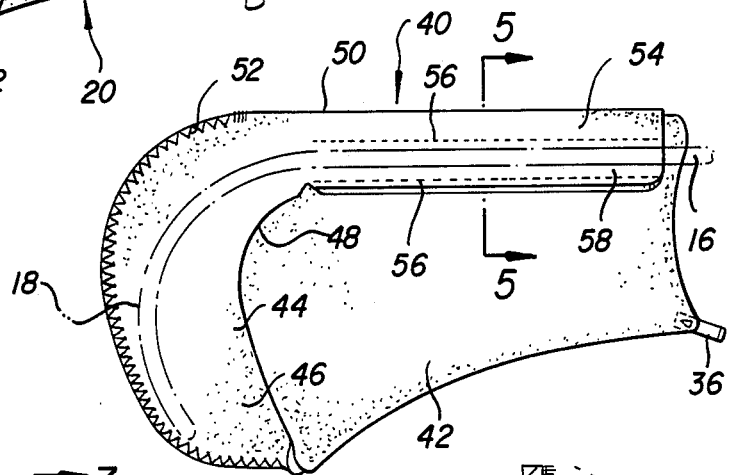
FIG. 4 is an elevational view similar to FIG. 2 showing a modified form of protector including an enlongated sleeve for receiving the temple.

Reference is now made to FIGS. 4 and 5 wherein there is illustated a modified form of protector generally identified by the numeral 40. The protector 40 includes an outer panel 42 and an inner panel 44. The inner panel 44 includes a rear portion 46 configurated to define in conjunction with the outer panel 42 an ear receiving pocket 48. It will be seen that the inner panel 44 is integrally formed with the outer panel 42 and connected thereto primarily along a longitudinal fold line 50. The rear portions of the panels 42, 44 are secured together by stitching 52.

In lieu of the cuts 36 and the straps 32, 34, defining the short sleeves, a narrow longitudinally extending portion 54 of the inner panel 44 is secured to the outer panel 42 by two rows of stitching 56. The stitching 56 defines an elongated sleeve 58 in the manner best shown in FIG. 5.

It is to be noted that the sleeve 56 terminates short of the front edge of the outer panel 42 so that it may abut against the rear face of a lens 14 or the like portion of the frame of the glasses.

Further, in order to facilitate the stabilization of the lower front cover of the protector with respect to the glasses, the lower front corner of the outer panel 42 is provided with one of the clips 37.

Figure 6:
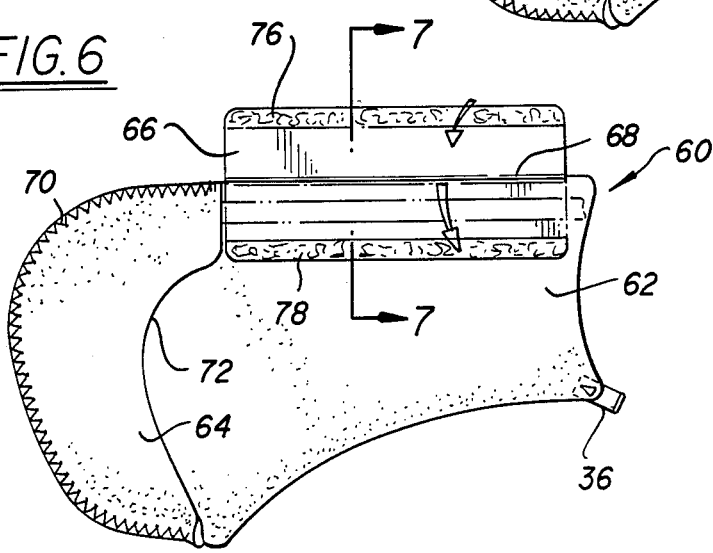
FIG. 6 is yet another elevational view of a modified form of protector wherein the elongated sleeve for receiving the temple is hinged relative to the outer panel so as to facilitate the mounting of the protector on glasses.
Figure 7:
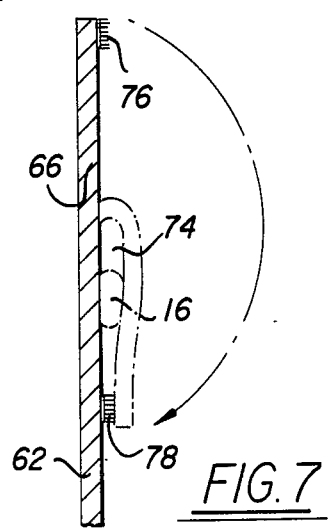
FIG. 7 is an enlarged fragmentary transverse vertical sectional view taken generally along the line 7—7 of FIG. 6 and shows more the details of the means for forming the elongated sleeve.

With respect to FIGS. 6 and 7, there is illustrated a still further form of protector, generally identified by the numeral 60. The protector 60 is generally a combination of the protector 20 and the protector 40. The protector 60 includes an outer panel 62 which will be of the same general configuration as the outer panel 42. However, in lieu of a one piece inner panel, there is a separately formed rear inner panel 64 and a longitudinally extending forward inner panel 66 which is formed integrally with the outer panel 62 and connected thereto generally along a fold line 68.

The rear inner panel 64 is secured about its periphery to a like periphery of the rear portion of the outer panel 62 such as by stitching 70. The rear inner panel 64 together with the rear portion of the outer panel 62 defines an ear receiving pocket 72.

The inner panel 66, when folded relative to the outer panel 62 as shown in phantom lines in FIG. 7, defines sleeve means 74 for receiving a temple of glasses, such as the temple 16.

In order that the inner panel 66 may form the sleeve means 74, which is in the form of an elongated sleeve, the free edge of the panel 66 parallel to the fold line 68 is provided with a self-adhering connector 76. A like line of self-adhering connector 78 is carried by the inner surface of the outer panel 62. The connectors 76, 78 are of an arrangement wherein they releasably interlock with one another for repeated engagement. The connectors 76, 78 may be of the well known "VELCRO". It will be readily apparent that this construction permits the mounting of the protector 60 on a temple with ease.

The lower forward corner of the outer panel 62 may be provided with a clip 37 as previously described.

While the protectors may be primarily utilized by skiers, it is to be understood that the utilization is not so limited in that the protectors could be utilized by hikers, bike riders, and other sports and occupations where the wearer is exposed to wind and sun. Further, in order that the protectors may have certain thermal qualities as well as merely shielding function, the various panels may be formed of an insulating cloth and may be of a laminated construction.

Although only several preferred embodiments of the protector have been specifically illustrated and described herein, it is to be understood that minor variations may be made in the protectors without departing from the spirit and scope of the invention as defined by the appended claims.

I claim:

1. A combination sun shade and face, eye and ear protector, said protector comprising an outer panel having a length substantially greater than its width and adapted to extend along substantially all of a temple portion of a pair of glasses, said outer panel having a rear portion, an inner panel, said panels having top, rear and bottom edges, means securing said top, rear and bottom panel edges together to form an ear receiving pocket, and mounting means carried by said outer panel for mounting said protector on the temple of the wearer's glasses.

2. A protector according to claim 1 wherein said mounting means are in the form of sleeve means.

3. A protector according to claim 2 wherein said sleeve means are in the form of a pair of longitudinally spaced short sleeves each defined by a strap formed by a pair of transverse cuts and one of said straps is disposed generally within said ear receiving pocket.

4. A protector according to claim 2 wherein said sleeve means is in the form of an elongated sleeve extending forwardly from the vicinity of said ear receiving pocket.

5. A protector according to claim 2 wherein said sleeve means is in the form of an elongated sleeve extending forwardly from the vicinity of said ear receiving pocket on an inner side of said outer panel.

6. A protector according to claim 5 wherein said elongated sleeve is in part defined by a forward extension of said inner panel.

7. A protector according to claim 5 wherein said elongated sleeve is in part defined by a forward extension of said inner panel with said elongated sleeve being defined by two longitudinal rows of securement.

8. A protector according to claim 5 wherein said elongated sleeve is in part defined by a forward extension of said inner panel with said elongated sleeve being defined by two longitudinal rows of stitching.

9. A protector according to claim 5 wherein said elongated sleeve is in part defined by a forward extension of said inner panel formed integrally with said outer panel and reversely folded relative to said outer panel, and at least one longitudinal line of securement between said outer panel and said forward extension.

10. A protector according to claim 9 wherein said line of securement is of the separable and re-engagement type to facilitate mounting of said protector on a temple.

11. A protector according to claim 5 wherein said inner panel and said forward extension are integrally connected to one another and to said outer panel.

12. A protector according to claim 5 wherein said inner panel and said forward extension are separately formed with said forward extension being integrally connected to said outer panel.

13. A protector according to claim 1 wherein said protector is formed of a cloth having insulating characteristics.

14. A protector according to claim 1 wherein said outer panel has a lower forward corner, and a glasses engaging clip is carried by said lower forward corner.

* * * * *